United States Patent [19]

Nakanishi et al.

[11] Patent Number: 4,868,159

[45] Date of Patent: Sep. 19, 1989

[54] NOVEL SUBSTANCES KS-501 AND KS-502 AND PROCESS FOR THEIR PREPARATION

[75] Inventors: Satoshi Nakanishi; Koji Yamada, both of Machida; Isao Kawamoto, Hiratsuka; Katsuhiko Ando, Machida; Hiroshi Sano, Machida; Toru Yasuzawa, Machida; Hiroshi Kase, Koganei, all of Japan

[73] Assignee: Kyowa Hakko Kogyo Co., Ltd., Tokyo, Japan

[21] Appl. No.: 165,738

[22] Filed: Mar. 9, 1988

[30] Foreign Application Priority Data

Mar. 10, 1987 [JP] Japan .................................. 62-54365
Mar. 10, 1987 [JP] Japan .................................. 62-54366

[51] Int. Cl.$^4$ ..................... C12P 19/44; C07G 3/00; C07H 15/00
[52] U.S. Cl. ..................................... 514/25; 435/74; 536/4.1; 536/18.2
[58] Field of Search .................... 435/254, 79, 78, 911, 435/74; 536/18.2, 4.1; 514/25

[56] References Cited

U.S. PATENT DOCUMENTS 3,781,267 12/1973 Jaques et al. ...................... 536/18.2
4,112,075 9/1975 Baschang et al. .................... 514/25

FOREIGN PATENT DOCUMENTS 2174696A 11/1986 United Kingdom ............... 536/18.2

OTHER PUBLICATIONS

*Chemical Abstracts*, vol. 100, 1984, p. 417, Abstract No. 207601a, Takata, M., "Correlations Among Culture Times, Sugar Composition and Biological Activities of Aporothrix s. Antigens".
Chemical Abstracts, vol. 91, 1979, p. 3726, Abstract No. 3729g; Nakamura, Y., "Purification and Isolation of a Biologically Active Peptido-Rhamnogalactan from *Sporothrix s*".
Chem. Pharm. Bull., 28, 3157–3162 (1980), Ninomiya, Y. T. et al.
J. Antibiot., 37, 469–474 (1984), Umehara, K. et al.
Agric. Bio. Chem., 50, 2723–2727 (1986), Oka, S. et al.
J. Antibiot., 37, 1153–1160 (1984), Umehara, K. et al.

*Primary Examiner*—Johnnie R. Brown
*Assistant Examiner*—Pamela S. Webber
*Attorney, Agent, or Firm*—Michael N. Meller

[57] ABSTRACT

Novel physiologically active substances KS-501 and KS-502 having inhibitory activity on serotonin release from platelets and/or platelet aggregation are produced by culturing a microorganism of the genus Sporothrix.

4 Claims, No Drawings

NOVEL SUBSTANCES KS-501 AND KS-502 AND PROCESS FOR THEIR PREPARATION

BACKGROUND OF THE INVENTION

The present invention relates to novel substances capable of inhibiting serotonin release from platelets and/or platelet aggregation which are produced by a microorganism belonging to the genus Sporothrix, a process for preparing the same and a pharmaceutical composition containing the same.

Products of a large number of microorganisms obtained from nature have been studies with a view to providing useful novel physiologically active substances which can be used as pharmaceuticals or intermediates therefor. As a result, it has been found that physiologically active substances capable of inhibiting serotonin release from platelets and/or platelet aggregation are produced in the culture of a newly isolated microorganism. After isolation and purification of the substances from the culture, their physicochemical properties have been investigated, whereby the substances have been found to be novel physiologically active substances. The substances are hereinafter referred to as KS-501 and KS-502.

As the substances capable of inhibiting serotonin release from platelets or platelet aggregation which are produced by microorganisms, the following compounds have been reported.

Pyrrothines

Chem. Pharm. Bull. 28, 3157–3162 (1980)

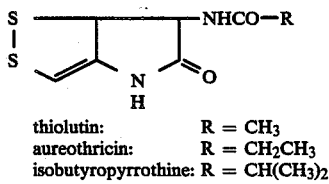

thiolutin: R = CH₃
aureothricin: R = CH₂CH₃
isobutyropyrrothine: R = CH(CH₃)₂

WF-5239

J. Antibiot. 37, 469–474 (1984)

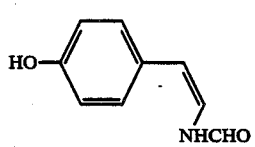

WF-30581

J. Antibiot. 37, 1153–1160 (1984)

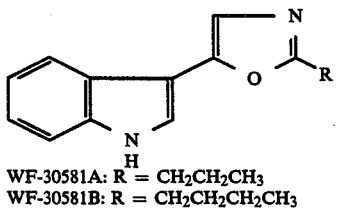

WF-30581A: R = CH₂CH₂CH₃
WF-30581B: R = CH₂CH₂CH₂CH₃

KS-290IIi-2

Japanese Published Unexamined Patent Application No. 195689/86

Staurosporine

Agric. Biol. Chem. 50, 2723–2727 (1986)

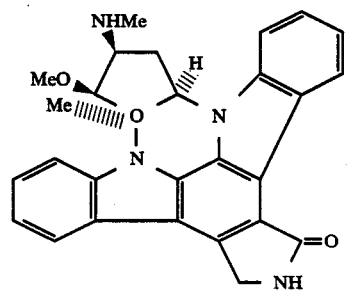

Results of the recent research of the function of serotonin released from platelets suggest that serotonin released from platelets contributes to platelet aggregation and contraction of vessels, especially cerebral vessels. Therefore, substances inhibiting serotonin release from platelets, as well as substances inhibiting platelet aggregation, are considered to be useful as antithrombotic agents, especially those for cerebral thrombosis. That is, KS-501 and KS-502 are expected to be useful for treating thrombosis, especially cerebral thrombosis such as cerebral ischemic attack.

SUMMARY OF THE INVENTION

According to the present invention, novel physiologically active substances KS-501 and/or KS-502 are produced by culturing a microorganism belonging to the genus Sporothrix and being capable of producing KS-501 and/or KS-502 in a culture medium until KS-501 and/or KS-502 are accumulated in the culture, and recovering KS-501 and/or KS-502 therefrom. KS-501 and KS-502 have an inhibitory activity on serotonin release from platelets and/or platelet aggregation.

Detailed Description of the Invention

The physicochemical properties of KS-501 and KS-502 are given below:

| State: | white powder |
|---|---|
| Melting point: | 149–152° C. |
| Specific rotation: | $[\alpha]_D^{23}$ −53° (c = 0.3, methanol) |
| Solubility: | |
| Readily soluble: | chloroform, ethyl acetate, acetonitrile, methanol, n-butanol, acetone, tetrahydrofuran, dioxane, dimethylsulfoxide, pyridine, monoethanolamine, acetic acid, alkaline water |
| Insoluble: | hexane, carbon tetrachloride, benzene, neutral water, acidic water |
| Color reaction: | Positive in reactions with iodine, anisaldehyde and ferric chloride; negative in reaction with anilinephthalic acid and ninhydrin and Reiden-Smith reactions. |

Ultraviolet absorption spectrum:
Acidic and neutral methanol solution: $\lambda_{max}$ ($\epsilon$)
254 nm (6760), 278 nm (5560, sh)
Alkaline methanol solution: $\lambda_{max}$ ($\epsilon$)

234 nm (16100, sh), 292 nm (11500)
Infrared absorption spectrum: KBr
3380, 2960, 2924, 2852, 1722, 1608, 1586, 1466, 1323, 1264, 1168, 1149, 1129, 1064, 996 cm$^{-1}$
Mass spectrum: SIMS, positive m/z 605 (M+H)$^+$, 443, 235
$^1$H-NMR (400 MHz, CD$_3$OD, δ): 6.58 (1H, d, J=2.1Hz), 6.55-6.50 (3H, m), 6.38 (1H, d, J=2.1Hz), 5.55 (1H, d, JH=1.8Hz), 4.28 (1H, dd, J=3.9, 1.8Hz), ca. 4.1 (2H), 3.76 (1H, br t, J=6.4Hz), 3.65 and 3.61 (AB in ABX, J$_{AB}$=11.2, J$_{AX}$=5.8, J$_{BX}$=7.0Hz), 2.65 (2H, br dd), 2.56 (2H, br dd), ca. 1.6 (4H, m), 1.2-1.4 (16H), 0.90 (3H, t, J=6.9Hz), 0.88 (3H, t, J=7.1Hz)
$^{13}$C-NMR (100 MHz, CD$_3$OD, δ): 168.8, 161.1, 159.3, 157.2, 153.1, 146.7, 144.7, 116.3, 114.0, 113.8, 111.1, 108.4, 107.5, 102.0, 85.5, 83.6, 78.6, 72.2, 64.4, 36.8, 34.9, 33.0 (2), 32.6, 32.4, 306., 30.3 (3), 23.7 (2), 1.4. (2)

Rf values in thin layer chromatography of KS-501 with various developing agents are shown in Table 1. The detection was carried out under ultraviolet lamp at 253.7 nm.

TABLE 1

| Silica gel thin layer chromatography of KS-501 | |
|---|---|
| Developing Agent | Rf Value |
| Chloroform:methanol = 7:3 (V/V) | 0.49 |
| Chloroform:methanol: conc. ammonia water = 19:5:1 (V/V/V) | 0.08 |
| Acetone | 0.51 |

Thin layer: silica gel 60 F$_{254}$ plate (Merck Inc., 5628)
Development: room temperature, ascending method, 15 to 30 minutes

KS-502

| State: | white powder |
|---|---|
| Melting point: | 119-120° C. |
| Specific rotation: | [α]$_D^{23}$ −45° (c = 0.3, methanol) |
| Solubility: | |
| Readily soluble: | methanol, n-butanol, acetone, tetrahydrofuran, dioxane, dimethylsulfoxide, pyridine, monoethanolamine, acetic acid, alkaline water |
| Soluble: | chloroform, ethyl acetate, acetonitrile |
| Insoluble: | hexane, carbon tetrachloride, benzene, neutral water, acidic water |
| Color reaction: | Positive in-reactions with iodine, anisaldehyde and ferric chloride; negative in reaction with anilinephthalic acid and ninhydrin and Reiden-Smith reactions. |

Ultraviolet absorption spectrum:
Acidic and neutral methanol solution: λ$_{max}$(ε) 252 nm (14100), 282 nm (6600, sh), 300 nm (5400, sh)
Alkaline methanol solution: λ$_{max}$ (ε) 234 nm (18900, sh), 298 nm (24800)
Infrared absorption spectrum: KBr
3450, 2972, 2940, 2872, 1724, 1595, 1463, 1432, 1375, 1343, 1245, 1161, 1135, 1062 cm$^{-1}$
Mass spectrum: SIMS, negative m/z 647(M-1)$^{-1}$, 393, 251
$^1$H-NMR (400 MHz, CD$_3$OD, δ): 6.60 (1H, d, J=2.3Hz), 6.58 (1H, d, J=2.1Hz), 6.51 (1H, d, J=2.3Hz), 6.38 (1H, d, J=2.1Hz), 5.54 (1H, d, J=1.8Hz), 4.27 (1H, dd), ca. 4.1 (2H), 3.76 (1H, br t, J=5.9Hz), 3.65 and 3.61 (2H, AB in ABX, J$_{AB}$=11.0, J$_{AX}$=5.6, J$_{BX}$=7.0Hz), 3.09 (2H, br dd), 2.65 (2H, br dd), ca. 1.6 (4H, m), 1.2-1.4 (16H), 0.88 (3H, t, J=6.6Hz), 0.87 (3H, t, J=6.7Hz)
$^{13}$C-NMR (100 MHz, CD$_3$OD, δ): 176.6, 168.2, 164.3, 161.2, 157.3, 154.6, 149.6, 144.8, 116.0, 115.7, 115.6, 111.1, 108.6, 108.4, 102.0, 85.5, 83.5, 78.6, 72.2, 64.4, 36.5, 34.9, 33.2, 33.1, 33.0, 32.6, 31.0, 30.7, 30.5, 30.3, 23.74, 23.70, 14.46, 14.43

Rf values in thin layer chromatography of KS-502 with various developing agents are shown in Table 2. The detection was carried out under ultraviolet lamp at 253.7 nm.

TABLE 2

| Silica gel thin layer chromatography of KS-502 | |
|---|---|
| Developing Agent | Rf Value |
| Chloroform:methanol = 7:3 (V/V) | 0.31 |
| Chloroform:methanol: conc. ammonia water = 19:5:1 (V/V/V) | 0.00 |
| Acetone | 0.12 |

Thin layer: silica gel 60 F$_{254}$ plate (Merck Inc., 5628)
Development: room temperature, ascending method, 15 to 30 minutes From the physioco-chemical properties described above, KS-501 and SK-502 are considered to have the following structural formula.

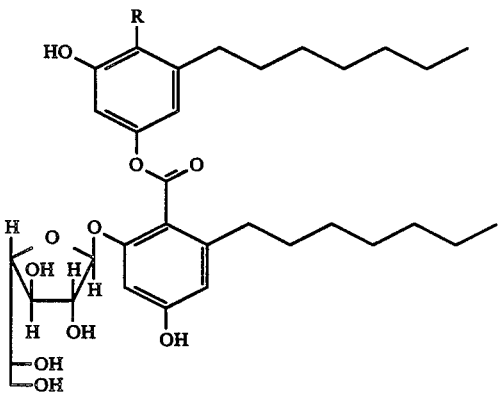

KS-501: R = H
KS-502: R = COOH

KS-501 and KS-502 have an inhibitory activity on serotonin release from platelets and KS-501 also has an inhibitory activity on platelet aggregation.

The process for preparing KS-501 and KS-502 is described below.

KS-501 and/or KS-502 can be prepared by culturing a microorganism belonging to the genus Sporothrix and having an ability to produce KS-501 and/or KS-502 in a medium until KS-501 and/or KS-502 are accumulated in the culture, and recovering KS-501 and/or KS-502 from the culture.

Any microorganism can be employed as a KS-501 and/or KS-502 producing microorganism, so long as it belongs to the genus Sporothrix and has an ability to produce KS-501 and/or KS-502. A preferred example is Sporothrix sp. KAC-1985 strain (hereinafter referred to as KAC-1985) isolated by the present inventors from fallen leaves collected in Yamakita-cho, Ashigarakami-gun, Kanagawa Prefecture, Japan.

KAC-1985 strain has the following mycological characteristics.

(1) Cultural characteristics

Cultural characteristics of the strain of malt extract agar medium and potato-glucose agar medium are as follows.

The growth is relatively slow. By culturing at 20° C. for 30 days, a diameter of colony reaches 29 to 33 mm. The colony shows a dome-like shape. The surface and the back side of the colony are both white or creamy.

A hypha has a septum and extends in and on the medium. The hypha has a diameter of 1 to 6 $\mu$m and is colorless, smooth and well branched. Sometimes fusion of hyphae is observed. A conidiophore is colorless and smooth, has a length of 4.5 to 20 $\mu$m and a width of 1.5 to 2.5 $\mu$m, and sometimes has septum. A conidium sympodially grows at the end of conidiophore and sometimes the conidiophore extends after the formation of conidium. The conidium is a single cell, which is colorless, smooth and long oval, and has a length of 4 to 7 $\mu$m, or in a few cases, to 10 $\mu$m and a width of 1 to 2 $\mu$m. No complete generation of this strain is observed.

(2) Physiological properties

Growth temperature: 5°–25° C.

Optimum growth temperature: 15°–25° C.

Growth pH: 3–11

Optimum growth pH: 4–9

Based on the foregoing mycological properties, identification of KAC-1985 was made according to The Genera of Fungi Sporulating in Pure Culture, 2nd ed Cramer, Vaduz, J.A. von Arx, 1974. As the result, this strain was identified as a strain belonging to Sporothrix sp. The strain was named Sporothrix sp. KAC-1985 and deposited with the Fermentation Research Institute, Agency of Industrial Science and Technology under FERM BP-1278 on Feb. 4, 1987.

Ordinary culturing procedures employed for the culturing of fungi are applicable to the culturing in the present invention. Either a natural medium or a synthetic medium can be used, so long as it contains appropriate amounts of carbon source, nitrogen source, inorganic matters, etc. which are assimilable by the microorganism used.

As the carbon source, carbohydrates such as glucose, fructose, stabilose, sucrose, lactose, starch, dextrin, mannose, maltose, molasses and an instant mashed potato; organic acids such as citric acid, malic acid, acetic acid and fumaric acid; amino acids such as glutamic acid; glycerol, cotton seed oil, etc. can be used.

As the nitrogen source, ammonium salts such as ammonium chloride, ammonium sulfate, ammonium nitrate and ammonium phosphate; amino acids such as aspartic acid, glutamine, cystine and alanine; urea, malt extract, peptone, meat extract, yeast extract, dry yeast, corn steep liquor, soybean powder, cotton seed cake, soybean casein, Casamino acids, pharmamedia, soluble vegetable protein, vegetable or fruit juice, etc. can be used.

As the inorganic matters, potassium dihydrogen phosphate, disodium hydrogen phosphate, magnesium sulfate, ferrous sulfate, manganese sulfate, cobalt sulfate, zinc sulfate, calcium phanthothenate, ammonium molybdate, aluminium potassium sulfate, barium carbonate, calcium carbonate, cobalt chloride, sodium chloride, magnesium phosphate, etc. can be used.

Furthermore, substances capable of promoting the propagation of microbial cells or the production of KS-501 and/or KS-502 such as vitamins and thiamine may be added to the medium, if required.

When the microorganism to be used requires specific substances for the growth, it is necessary to add the substances to the medium.

Culturing is carried out at a temperature of 15 to 25° C. at pH around neutrality by shaking culture, aeration-stirring culture, etc.

Maximum accumulation of KS-501 and/or KS-502 can be attained by culturing for 3 to 15 days, and the culturing is completed.

To isolate and recover KS-501 and/or KS-502 accumulated in the cells, ordinary procedures for the recovery of a physiologically active substance from cells can be employed.

That is, KS-501 and/or KS-502 can be isolated by collection of the cells through filtration, centrifugation, etc.; extraction from the cells with organic solvents such as methanol and acetone, etc.; partition with water or organic solvents; and adsorption and desorption of the active substance by column chromatography or thin layer chromatography using adsorptive resins, silica gel, silanized silica gel, aluminum, cellulose, diatomaceous earth, magnesium siliate, gel filtering agents, etc.

An example of the process for isolating KS-501 and/or KS-502 from the cells is given below.

The cells are collected by filtration or centrifugation of the culture. An organic solvent such as methanol is added to the obtained cells. After thoroughly stirring the mixture, the cells are separated from the mixture by filtration or centrifugation again. The obtained filtrate or supernatant is concentrated under reduced pressure to remove the solvent and to obtain an aqueous solution. Then, a water-immiscible solvent such as ethyl acetate is added to the aqueous solution to conduct extraction. The extract is concentrated under reduced pressure, and subjected to repetitions of silica gel chromatography using a mixed solvent of chloroform-methanol as a developing solvent. The methanol content is stepwise increased to elute KS-501 and/or KS-502.

In the case of the isolation of KS-501, fractions containing KS-501 are combined and concentrated under reduced pressure and the concentrate is dissolved in a small quantity of chloroform. The solution is allowed to stand at 0° C. for crystallization. The thus obtained crystals are recrystallized by the same procedure to give white powders of KS-501.

In the case of the isolation of KS-502, fractions containing KS-502 resulting from silical gel chromatography described above are combined and concentrated under reduced pressure and the concentrate is subjected to column chromatography using Sephadex LH-20 (product of Pharmacia Fine Chemicals, Inc.). Fractions containing KS-502 are combined and concentrated to dryness under reduced pressure to give white powders of KS-502.

During the said purification, detection of KS-501 and/or KS-502 is carried out by silica gel thin layer chromatography followed by the iodine reaction or ultraviolet irradiation of 253.7 nm.

KS-501 and KS-502 inhibit serotonin release from platelets and/or platelet aggregation and thus are expected to be useful as anti-thrombotic agents, especially those for cerebral thrombosis.

Thus, according to a further feature of the present invention, there is provided a pharmaceutical composition comprising, as active ingredient, effective amounts of KS-501 and/or KS-502 usually in association with at least one pharmaceutically acceptable carrier or excipient.

The pharmaceutical composition may be administered through oral or parenteral route (for example, injection, application, and inhalation). KS-501 and/or KS-502 can be administered as such, but generally administered in the form of tablets, pills, powder, granules, capsules, suppository, injection, etc. Conventional pharmaceutically acceptable carriers can be used for medical compositions of this invention. They include lactose, dextrose, sucrose, sorbital, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogensulfite, aluminium stearate, magnesium stearate, mineral oil, vegetable oil, white Vaseline®, liquid paraffin, etc., and can be appropriately selected in view of the kind of preparations.

Certain specific embodiments of the present invention are illustrated by the following examples.

EXAMPLE 1

Sporothrix sp. KAC-1985 was used as the seen strain. The strain was inoculated into 40 ml of a seed medium (pH 6.0, prior to sterilization) containing 1.0 g/dl glucose, 0.5 g/dl peptone (product of Kyokuto Pharmaceutical Industry Co., Ltd.), 0.5 g/dl dry yeast Ebios (product of Asahi Breweries, Ltd.), 0.2 dl/dl V-8 Vegetable Juice (product of Campbell Co.) and 0.3 g/dl calcium carbonate in a 300 ml-Erlenmyer flask and subjected to shaking culture at 25° C. until the strain sufficiently grew. Then, 10 ml of the seed culture was inoculated with 100 ml of a fermenation medium having the following composition.

Composition of the fermentation medium: 1.0 g/dl glucose, 0.5 g/dl peptone, 0.5 g/dl dry yeast Ebios, 0.2 dl/dl V-8 Vegetable Juice, 0.2 dl/dl apple juice (product of Meijiya) and 0.5 g/dl calcium carbonate (pH 6.0, prior to sterilization).

Culturing was carried out with shaking at 25° C. for 12 days. After the completion of culturing, 1.3 l of the culture was centrifuged at 7000 rpm using RPR-9-2 Model Rotor (product of Hitachi Ltd.). Then, 1.3 l of methanol was added to the cells, and after thorough stirring, the cells were removed by filtration. The thus obtained methanol extract was concentrated under reduced pressure to remove methanol and to obtain about 100 ml of an aqueous solution. After being adjusted to pH 2 with 2N hydrochloric acid, the solution was extracted with 100 ml each of ethyl acetate three times. The ethyl acetate layer was concentrated under reduced pressure and the concentrate was dissolved in a small quantity of chloroform. The solution was charged to a column packed with 250 ml of silica gel C-200 (product of Wako Pure Chemical Industries, Ltd.) suspended in chloroform and successively eluted with 500 ml each of chloroform, 5% methanol/chloroform (V/V) and 10% methanol/chloroform (V/V) as developing solvents. The eluted fractions were taken in 18 g portions, and KS-501 was eluted in fraction Nos. 121 to 136. These fractions were combined and concentrated under reduced pressure, and the concentrate was then dissolved in a small quantity of chloroform. The solution was charged to a column packed with 100 ml of silica gel C-300 (Wako Pure Chemical Industries, Ltd.) suspended in chloroform and successively eluted with 200 ml of chloroform, 300 ml of 5% methanol/chloroform (V/V), 300 ml of 7% methanol/chloroform (V/V) and 300 ml of 9% methanol/chloroform (V/V) as developing solvents. The eluted fractions were taken in 18 g portions, and KS-501 was eluted in fraction Nos. 38 to 59. These fractions were combined and concentrated to give 315 mg of a pale yellow oily substance. The oily substance was dissolved in about 5 ml of chloroform and crystallized at 0° C. The obtained crystals were dissolved again in chloroform and recrystallized at 0° C. to give 192 mg of KS-501 as white powders. During the foregoing steps, KS-501 was detected by silica gel thin layer chromatography followed by the iodine reaction or ultraviolet irradication at 253.7 nm.

EXAMPLE 2

Sporothrix sp. KAC-1985 was cultured in the same manner as in Example 1. After the completion of culturing, 1.3 l of the culture was centrifuged at 7000 rmp using RPR-9-2 Model Rotor. Then, 1.3 l of methanol was added to the cells, and after thorough stirring, the cells were removed by filtration. The thus obtained methanol extract was concentrated under reduced pressure to remove methanol and to obtain about 100 ml of an aqueous solution. After being adjusted to pH 2 with 2N hydrochloric acid, the solution was extracted with 100 ml each of ethyl acetate three times. the ethyl acetate layer was concentated under reduced pressure and the concentrate was dissolved in a small quantity of chloroform. The solution was charged to a column packed with 250 ml of silica gel C-200 suspended in chloroform and successively eluted with 500 ml each of chloroform, 5% methanol/chloroform (V/V), 10% methanol/chloroform (V/V) and 20% methanol/chloroform (V/V) as developing solvents. The eluted fractions were taken in 18 g portions, and KS-502 was eluted in fraction Nos. 160 to 201. These fractions were combined and concentrated under reduced pressure, and the concentrate was then dissolved in a small quantity of methanol. The solution was charged to a column packed with 100 ml of Sephadex LH-20 (product of Pharmacia Fine Chemicals Inc., suspended in methanol and eluted with methanol as a developing solvent. The eluted fractions were taken in 4.4 ml portions, and KS-502 was eluted in fraction Nos. 19 to 28. These fractions were combined and concentrated to dryness under reduced pressure to give 92 mg of KS-502 as white powders. During the foregoing steps, KS-502 was detected by silica gel thin layer chromatography followed by the iodine reaction or ultraviolet irradiation at 253.7 nm.

The inhibitory activities of KS-501 and KS-502 on serotonin release from platelets and/or platelet aggregation are explained below, referring to experimental examples.

Experimental Example 1

Effect on serotonin release from rabbit platelets
(1) Method 9.25 vol of blood was sampled from the carotid artery of a white rabbit and placed in a FALCON 2070 tube (product of Falcon, Bector Dickinson) containing 0.75 vol of 77 mM ethylenediaminetetraacetic acid (EDTA). The thus obtained blood was centrifuged at 200 x g for 15 minutes to obtain platelet rich plasma (referred to as PRP hereinafter). This PRP was incubated with [2-$^{14}$C]-serotonin (2 μCi/100 ml PRP) at 37° C. for an hour to incorporate [2-$^{14}$C]-serotonin therein. Then, the PRP was centrifuged at 650 x g for 15 minutes to obtain platelet precipitates. After washing with Tris-buffered physiological saline (pH 7.4, containing 1 mM EDTA), the platelet precipitates were suspended in CA$^{++}$-free Tyrode's soluton to reach a final density of $10^9$ cells/ml.

To 0.475 ml of the thus prepared [2-$^{14}$C]-serotoninlabeled platelet suspension was added 5 μl of a solution of the test compound. After incubation at 37° C. for 3 minutes, platelet activating factor (final concentration: 10$^{-9}$M) was added as a stimulant, followed by incubation for further 3 minutes. 0.3 ml of the reaction solution was immediately taken and poured into 30 μl of ice-cold 0.1 mM formaldehyde5 mM EDTA solution to terminate the reaction. After centrifugation at 3,000 rpm at 0° C. for 10 minutes, 250 μl of the supernatant was taken and the radioactivity was measured with a liquid scintillation counter.

Results

TABLE 3

| Compound | Concentration (μg/ml) | Rate of inhibition of serotonin release* (%) |
|---|---|---|
| KS-501 | 3.0 | 10.2 |
|  | 10.0 | 27.1 |
|  | 30.0 | 66.4 |
| KS-502 | 10.0 | 2.7 |
|  | 30.0 | 28.9 |
|  | 50.0 | 51.4 |

*The rate of inhibition of serotonin release was calculated according to the following equation.

$$\text{Rate of inhibition of serotonin release (\%)} = \left(1 - \frac{\text{Degree of release in the presence of a test compound}}{\text{Degree of release in the absence of test compound}}\right) \times 100$$

As shown in Table 3, KS-501 and KS-502 inhibited serotonin release from rabbit platelets, depending on the concentration.

Experimental Example 2

Effect on platelet aggreation of rabbit platelets (1) Method 8.5 vol of blood was sampled from the carotid artery of a white rabbit and placed in a FALCON 2070 tube (product of Falcon, Bector Dickinson) containing 1.5 vol of citrate-dextrose soluton (71 mM citric acid, 85 mM sodium citrate and 111 mM dextrose). The thus obtained blood was centrifuged at 200×g for 15 minutes to obtain PRP. This PRP was centrifuged at 650×g for 10 minutes to obtain platelet precipitates. After washing with Ca++-free Tyrode's solution containing 2 mM ethyleneglycol bis(2-aminoethylether) tetraacetic acid (EGTA), the platelet precipitates were again centrifuged at 650 ×g for 10 minutes and washed. The thus obtained platelet precipitates were suspended in Ca++-free Tyrode's solution containing 0.25% bovine serum albumin to reach a density of 5×10$^8$ cells/ml. After the washed platelet suspension was allowed to stand at room temperature for about 30 minutes, 1 mM CaCl$_2$ or 1 mM EGTA was added thereto and the mixture was allowed to stand for further 30 minutes. Then, platelet aggregation was measured.

The aggregation of platelets was determined using an aggregometer, AGGRETEC TE-500 (product of Erma Optical Co., Ltd.) to which the Born method was applied.

First, 10 μl of a test compound soluton was added to 0.2 ml of the washed platelet suspension, while stirring at 1,000 rmp and at 37° C. After incubation at 37° C. for 3 minutes, 10 μl of thrombin (final concentration: 0.05 U/ml) or platelet activating factor (final concentration: 10$^{-10}$ M) was added as a stimulant to initiate the reaction. The rate of inhibition of platelet aggregation of the test compound was calculated from the maximum aggregation rate obtained by the use of the test compound and the maximum aggregation rate obtained by the use of only the solvent used for dissolving the test compound, according to the following equation.

$$\text{Rate of inhibition of aggregation (\%)} = \frac{A - B}{A} \times 100$$

A : Maximum aggregation rate of the solvent alone
B : Maximum aggregation rate of the test compound (2) Results

TABLE 4

| Compound | Stimulant | IC$_{50}$* (μg/ml) |
|---|---|---|
| KS-501 | Thrombin | 57 |
|  | Platelet activating factor | 38 |

*Concentration of the test compound showing 50% inhibition.

As shown in Table 4, KS-501 inhibited platelet aggregation stimulated with thrombin and platelet activating factor.

What is claimed is:
1. A compound represented by the formula (I)

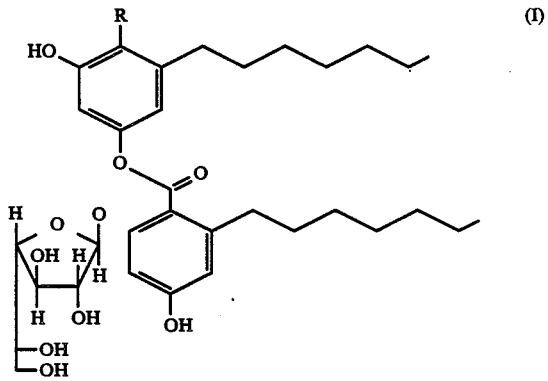

wherein R is hydrogen or carboxyl.

2. A process for preparing a compound as defined in claim 1, which comprises culturing a microorganism belonging to the genus Sporothrix in a medium until the compound is accumulated in the culture, and recovering the compound from the culture.

3. A process according to claim 2, wherein the microorganism is Sporothrix sp. KAC-1985 (FERM BP-1278).

4. A pharmaceutical composition comprising as active ingredient a serotonin release-inhibiting effective amount of a compound as defined in claim 1 in a pharmaceutically acceptable carrier or excipient.

* * * * *